(12) United States Patent
Somerson

(10) Patent No.: US 12,144,497 B2
(45) Date of Patent: Nov. 19, 2024

(54) SUTURE ANCHOR WITH REAL-TIME TENSION SENSOR

(71) Applicant: Board of Regents, The University of Texas System, Austin, TX (US)

(72) Inventor: Jeremy S. Somerson, League City, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 211 days.

(21) Appl. No.: 17/469,304

(22) Filed: Sep. 8, 2021

(65) Prior Publication Data

US 2022/0087671 A1 Mar. 24, 2022

Related U.S. Application Data

(60) Provisional application No. 63/080,478, filed on Sep. 18, 2020.

(51) Int. Cl.
*A61B 17/04* (2006.01)
*A61B 90/00* (2016.01)

(52) U.S. Cl.
CPC .. *A61B 17/0401* (2013.01); *A61B 2017/0409* (2013.01); *A61B 2017/0414* (2013.01); *A61B 2017/044* (2013.01); *A61B 2090/064* (2016.02); *A61B 2562/0214* (2013.01); *A61B 2562/0247* (2013.01)

(58) Field of Classification Search
CPC .... A61B 2017/0409; A61B 2017/0414; A61B 2017/044; A61B 2090/064
See application file for complete search history.

(56) References Cited

U.S. PATENT DOCUMENTS

| | | | | |
|---|---|---|---|---|
| 2001/0032517 A1* | 10/2001 | Reinemann, Jr. | ..... | G01L 5/0033 73/826 |
| 2006/0004364 A1* | 1/2006 | Green | ................. | A61B 17/064 606/313 |
| 2007/0088362 A1* | 4/2007 | Bonutti | ............. | A61B 17/7053 606/99 |
| 2010/0249777 A1* | 9/2010 | Sherman | ............. | A61B 5/1107 606/53 |
| 2011/0282361 A1* | 11/2011 | Miller | ................ | A61B 17/0401 606/139 |

(Continued)

*Primary Examiner* — Alexander J Orkin
(74) *Attorney, Agent, or Firm* — Thomas | Horstemeyer, LLP

(57) ABSTRACT

The present disclosure describes apparatuses and methods related to suture anchors. One such apparatus involves an inserter instrument for a suture anchor implant comprising a handle; a hollow outer barrel shaft extending from one end of the inserter instrument to an opposing end at an anchor screw attachment tip; and an inner barrel shaft extending along a length of the inserter instrument within a cavity of the hollow outer barrel shaft. The inserter instrument further includes a tension sensor coupled to an end of the inner barrel shaft, which can measure an amount of tension applied to an opposing end of the inner barrel shaft and output an electrical signal indicating a value of the measured tension, such that an electronic display communicatively coupled to the tension sensor can display the value of the measured tension indicated by the electrical signal.

5 Claims, 3 Drawing Sheets

(56) References Cited

U.S. PATENT DOCUMENTS

| | | | |
|---|---|---|---|
| 2014/0228880 A1* | 8/2014 | Bisson | A61B 17/0401 |
| | | | 606/232 |
| 2016/0367368 A1* | 12/2016 | Vidlund | A61F 2/2487 |
| 2018/0116821 A1* | 5/2018 | Johannaber | A61B 17/92 |
| 2018/0360448 A1* | 12/2018 | Harris | A61B 17/1114 |
| 2019/0201047 A1* | 7/2019 | Yates | A61B 18/1445 |

* cited by examiner

SUTURE ANCHOR WITH REAL-TIME TENSION SENSOR

CROSS-REFERENCE TO RELATED APPLICATION

This application claims priority to U.S. provisional application entitled, "Suture Anchor with Real-Time Tension Sensor," having Ser. No. 63/080,478, filed Sep. 18, 2020, which is entirely incorporated herein by reference.

BACKGROUND

Suture anchors are useful fixation devices for fixing tendons and ligaments to bone. Typically, a suture anchor is made up of an anchor screw, an eyelet, and a suture, in which the anchor (also referred to as an anchor implant) may be inserted into the bone and fastened to the bone using a screw mechanism or an interference fit. Correspondingly, the eyelet is a hole or loop in the anchor through which a suture can pass and connect the anchor to the suture, in which the suture is a thread material that can be used to attach tissues, such as tendons or ligaments, to the bone.

The anchor can be inserted into the bone using an inserter instrument with the anchor (and the suture loaded on the anchor) attached on a distal end of the inserter instrument. After the anchor is implanted in a drilled hole of the bone, the suture may be tensioned to a desired level by pulling on one or more free ends of the suture. The anchor may be designed to be deployed based on a certain amount of tension being supplied by a practitioner to the anchor via the suture connected to the anchor. However, over or under tensioning which may cause the anchor to be pulled out of its desired positioning or may result in the anchor not being properly engaged in the bone hole. Further, a certain level of tensioning may be required to be applied to the suture(s) in order to properly fasten tissues to the bone. As such, over or under tensioning of sutures is a safety risk.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

An improved inserter instrument for suture anchors is presented within the present disclosure. In one embodiment, a tension sensor and display are integrated into the inserter instrument which can give a practitioner the ability to pull a specific amount of tension on sutures that is confirmed via a readout on the display so that the tension can be adjusted to a proper value in real-time in accordance with the current tension reading on the display. Thus, while at present, surgeons do not have objective feedback about the amount of tension placed on body tissues when pulling suture anchors tight, the improved inserter instrument can prevent over-tensioning, such as at the rotator cuff where over-tensioning of sutures has been shown to cause tissue damage during rotator-cuff surgeries. Likewise, the improved inserter instrument can also prevent under-tensioning below a desired tension level by displaying the current value of tension being applied via the inserter instrument to the practitioner.

Figure 1:
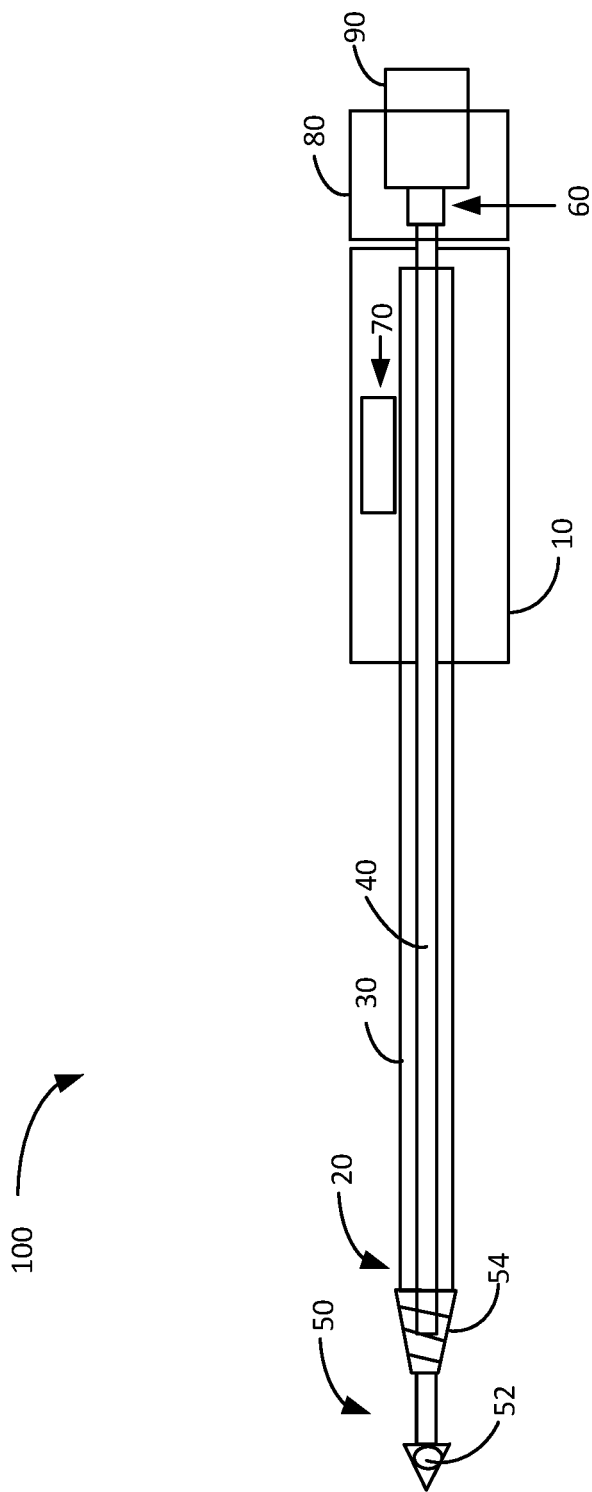
FIG. 1 shows an exemplary inserter instrument in accordance with various embodiments of the present disclosure.

Correspondingly, FIG. 1 shows an exemplary inserter instrument 100 in accordance with various embodiments of the present disclosure. The inserter instrument 100 includes an inserter handle 10 at one end and a screw attachment tip 20 at the opposing end. A hollow outer barrel shaft 30 extends from one end of the inserter instrument 100 to an opposing end at the screw attachment tip 20. Within a cavity of the hollow outer barrel shaft, an inner barrel shaft 40 extends along a length of the inserter instrument 100 such that a tip of the inner barrel shaft 40 may be threaded to screw securely into a suture anchor implant 50. For the figure, the anchor implant 50 is shown attached to the screw attachment tip 20. The anchor implant 50 is composed of an eyelet 52 and an anchor screw 54.

Figure 2:
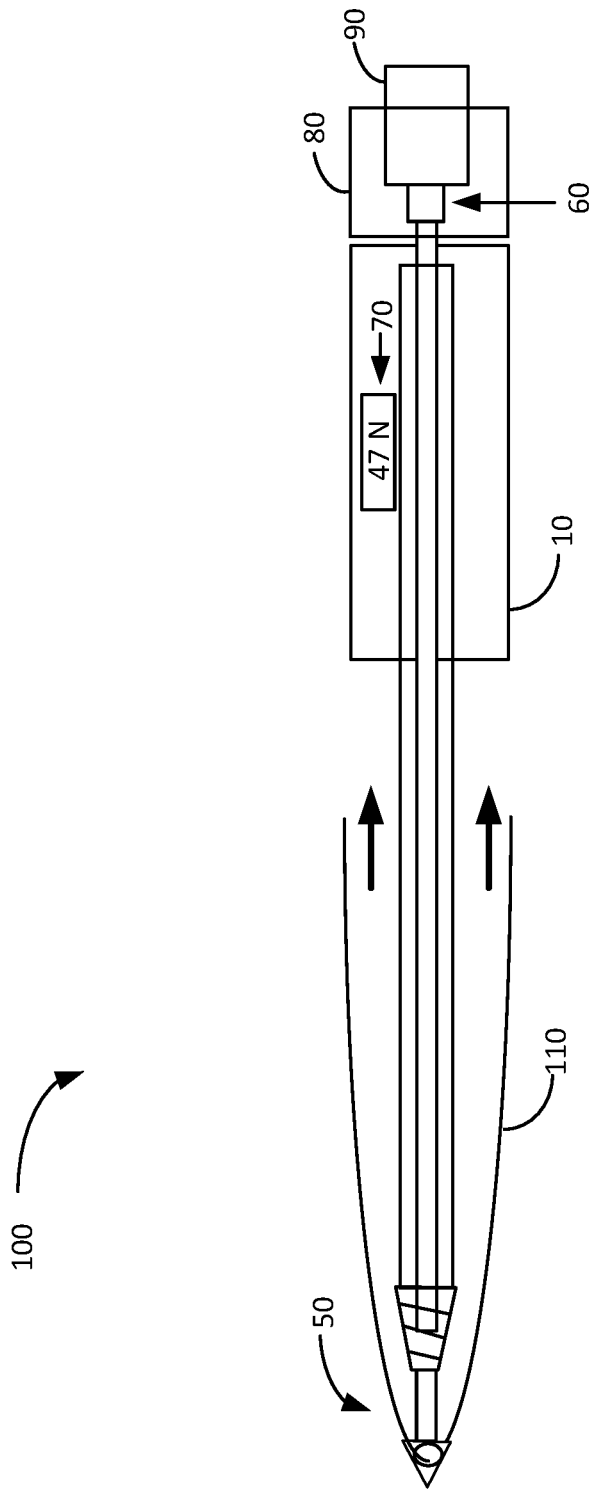
FIGS. 2-3 show the inserter instrument of FIG. 1 with tension being applied to a suture and a readout being displayed in accordance with various embodiments of the present disclosure.

Referring to FIG. 2, a suture 110 can be pulled through the eyelet 52 at a tip of the anchor implant 50. In practice, the suture may be tensioned by a practitioner (e.g., a surgeon) pulling free ends of the suture 100. When the suture is pulled, the pulling force pushes the inner barrel shaft 40 against a tension sensor 60 of the inserter instrument 100. In various embodiments, the tension sensor 60 measures an amount of tension in one or more sutures applied to the anchor implant 50 and thus, the inner barrel shaft 40 engages with the anchor implant. In various embodiments, the tension sensor 60 may be in the form of a capacitive sensor, optical sensor, piezo-electric sensor, pressure or force-sensing resistance type sensor, or electromechanical sensor, among others.

Figure 3:
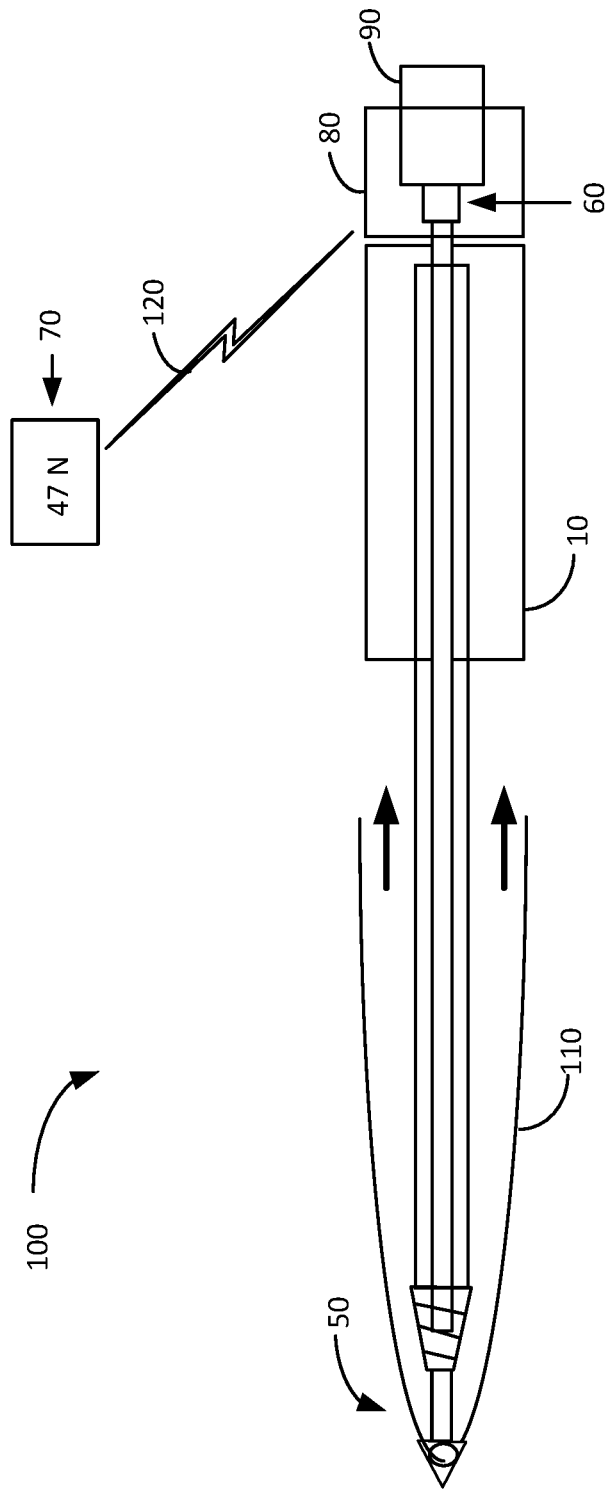

As discussed, in various embodiments, the tension sensor 60 is coupled to an end of the inner barrel shaft, wherein the tension sensor 60 is configured to measure an amount of tension applied to an opposing end of the inner barrel shaft and output an electrical signal indicating a value of the measured tension. As shown in FIG. 2, the resulting tension or force (e.g., 47 Newtons) may be shown on a read out display 70 (in real-time) that is electrically and/or communicatively coupled to the tension sensor 60 (and receives the electrical signal indicating the value of the measured tension). In various embodiments, the display 70 can be positioned along, but is not limited to being on, an exterior side of the handle 10, as shown in FIGS. 1-2. In other embodiments, the display 70 may be positioned in a different position, such as on an exterior end of the handle 10. Alternatively, as illustrated in FIG. 3, the electronic display 70 may be positioned remotely from the tension sensor 60 and may be in wireless communications, via a communication link 120, with the tension sensor 60 (e.g., via Bluetooth, Wi-Fi network, or other form of wireless communication technology), wherein the tension sensor 60 transmits tension force data to the electronic display 70. Additionally, a suture can be locked onto a suture cleat or tab (on the handle) to maintain the tension (that is output on the display 70). In various embodiments, the cleat may be positioned on a side or an end of the handle 10 and is configured to secure a suture that runs from the anchor implant 50 from unraveling or loosening.

In accordance with various embodiments of the present disclosure, the anchor screw 54 may be advanced by turning a knob 80 positioned at the end of the handle 10 and coupled to the outer barrel shaft 30. In one embodiment, a distal tip of the outer barrel shaft 30 has, but is not limited to having, a hex driver head that engages and advances the screw 54 but can disengage from the screw 54 when the handle 10 is pulled by the practitioner. An inner knob 90 at the end of the handle 10 (coupled to the inner barrel shaft 40) may be turned to release the anchor implant 50 from engagement with the inner barrel shaft 40.

The present disclosure also provides exemplary methods administering a suture anchor implant. One such method comprises attaching an anchor implant 50 to a screw attachment tip 20 of a hollow outer barrel shaft 30 of an inserter instrument 100, wherein the inserter instrument 100 comprises an inner barrel shaft 40 that is contained within a cavity of the outer barrel shaft 30 and engages with an interior portion of the anchor implant 50 wherein a suture is connected to an eyelet 52 of the anchor implant 50; and pulling the suture that is connected to the eyelet 52 of the anchor implant 100, thereby applying a tension to a distal end of the inner barrel shaft 40 of the inserter instrument 100, wherein a tension sensor 60 is coupled to an opposing end of the inner barrel shaft 40 that is proximal to a handle 10 of the inserter instrument 100. The method further comprises measuring a current force that is being applied to the inner barrel shaft 40 of the inserter instrument 100; and displaying a value of the current force on an electrical display 70 that is communicatively coupled with the tension sensor 60 of the inserter instrument 100.

Other aspects of an exemplary method can further include steps and/or features related to inserting the anchor implant within a hole in a bone of a patient via the inserter instrument; twisting the anchor implant within the hole via a turning motion of an outer barrel shaft of the inserter instrument; wherein the tension sensor comprises a capacitive sensor, an optical sensor, a piezo-electric sensor, a force-sensing resistance type sensor, or an electromechanical sensor; wirelessly sending a signal indicative of the value of the current force from the tension sensor to the electronic display; wherein the electronic display resides on an exterior of the handle; and/or wherein the electronic display is electrically coupled to the tension sensor.

It should be emphasized that the above-described embodiments are merely possible examples of implementations, merely set forth for a clear understanding of the principles of the present disclosure. Many variations and modifications may be made to the above-described embodiment(s) without departing substantially from the principles of the present disclosure. For example, an exemplary inserter instrument may contain additional features or modifications, such as inclusion of a thumb pad. All such modifications and variations are intended to be included herein within the scope of this disclosure.

Therefore, at least the following is claimed:

1. An inserter instrument for an anchor implant comprising:
   a handle;
   a hollow outer barrel shaft extending from one end of the inserter instrument to an opposing end at a suture anchor attachment tip;
   an inner barrel shaft extending along a length of the inserter instrument within a cavity of the hollow outer barrel shaft, wherein a distal end of the inner barrel shaft extends into a cavity of the suture anchor attachment tip and is configured to engage an implant suture anchor that is received by the suture anchor attachment tip;
   a tension sensor directly coupled to a proximal end of the inner barrel shaft, wherein the tension sensor is configured to measure an amount of tension applied to an opposing end of the inner barrel shaft via the implant suture anchor and output an electrical signal indicating a value of the measured tension; and
   an electronic display communicatively coupled to the tension sensor and configured to display the value of the measured tension indicated by the electrical signal.

2. The inserter instrument of claim 1, wherein the tension sensor comprises a capacitive sensor, an optical sensor, a piezo-electric sensor, a force-sensing resistance type sensor, or an electromechanical sensor.

3. The inserter instrument of claim 1, wherein the implant suture anchor comprises an anchor screw implant physically coupled to the suture anchor attachment tip.

4. The inserter instrument of claim 1, wherein the electronic display is positioned on an exterior of the handle, wherein the electronic display is electrically coupled to the tension sensor.

5. The inserter instrument of claim 1, wherein the electronic display is configured to be in wireless communication with the tension sensor.

* * * * *